US012773261B2

(12) United States Patent
Simani et al.

(10) Patent No.: US 12,773,261 B2
(45) Date of Patent: Oct. 27, 2026

(54) ROTATABLE SNARES AND RELATED METHODS

(71) Applicant: Boston Scientific Scimed, Inc., Maple Grove, MN (US)

(72) Inventors: Heather A. Simani, Dedham, MA (US); Tara E. Deland, Ann Arbor, MI (US); Kenneth R. Keene, Winchester, MA (US); Michael Powers, Pepperell, MA (US); Mickael A. Jette, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 181 days.

(21) Appl. No.: 18/766,773

(22) Filed: Jul. 9, 2024

(65) Prior Publication Data

US 2024/0358431 A1 Oct. 31, 2024

Related U.S. Application Data

(63) Continuation of application No. 17/690,949, filed on Mar. 9, 2022, now Pat. No. 12,059,198, which is a continuation of application No. 15/811,747, filed on Nov. 14, 2017, now Pat. No. 11,304,747.

(60) Provisional application No. 62/422,674, filed on Nov. 16, 2016.

(51) Int. Cl.

| | |
|---|---|
| ***A61B 18/14*** | (2006.01) |
| *A61B 17/29* | (2006.01) |
| *A61B 17/3205* | (2006.01) |
| *A61B 18/00* | (2006.01) |

(52) U.S. Cl.

CPC ........ *A61B 18/149* (2013.01); *A61B 18/1492* (2013.01); *A61B 2017/2929* (2013.01); *A61B 17/32056* (2013.01); *A61B 2018/00184* (2013.01); *A61B 2018/00202* (2013.01); *A61B 2018/0091* (2013.01);

(Continued)

(58) Field of Classification Search

CPC ............. A61B 18/149; A61B 18/1492; A61B 17/32056; A61B 2017/2929; A61B 2018/00184; A61B 2018/00202; A61B 2018/0091; A61B 2018/1407; A61B 2018/141; A61B 2018/1475

See application file for complete search history.

(56) References Cited

U.S. PATENT DOCUMENTS 6,352,539 B1 * 3/2002 Avellanet .................. B21C 1/02 606/113

2005/0159648 A1 7/2005 Freed (Continued)

*Primary Examiner* — Michael F Peffley
*Assistant Examiner* — Bo Ouyang
(74) *Attorney, Agent, or Firm* — Bookoff McAndrews PLLC

(57) ABSTRACT

A medical device may include a handle, a sheath fixed relative to the handle, a longitudinal actuator movable relative to the handle, an end effector, a member extending proximally from the end effector through the sheath, with a portion of the member being fixed relative to the longitudinal actuator, and a rotation actuator. Movement of the rotation actuator may cause rotation of the member relative to the sheath, and movement of the longitudinal actuator may cause longitudinal movement of the member relative to the rotation actuator.

20 Claims, 4 Drawing Sheets

(52) U.S. Cl.
CPC . *A61B 2018/1407* (2013.01); *A61B 2018/141* (2013.01); *A61B 2018/1475* (2013.01)

(56) References Cited

U.S. PATENT DOCUMENTS

| | | | | |
|---|---|---|---|---|
| 2009/0036899 | A1 * | 2/2009 | Carlton ............ | A61B 17/32056 606/29 |
| 2009/0112225 | A1 * | 4/2009 | Kaneko ............ | A61B 17/32056 606/113 |
| 2014/0277049 | A1 | 9/2014 | Rethy et al. | |
| 2017/0245909 | A1 | 8/2017 | Konesky et al. | |

* cited by examiner

ROTATABLE SNARES AND RELATED METHODS

CROSS-REFERENCE TO RELATED APPLICATION(S)

This patent application is a continuation of U.S. patent application Ser. No. 17/690,949, filed on Mar. 9, 2022, which is a continuation of U.S. patent application Ser. No. 15/811,747, filed on Nov. 14, 2017, now U.S. Pat. No. 11,304,747, issued on Apr. 19, 2022, which claims the benefit under 35 U.S.C. § 119 to U.S. Provisional Patent Application No. 62/422,674, filed on Nov. 16, 2016, each of which is incorporated by reference herein in its entirety.

TECHNICAL FIELD

Examples of the present disclosure relate generally to rotatable medical devices. In particular, examples of the present disclosure relate to rotatable snare devices.

BACKGROUND

Medical devices, such as endoscopes or other suitable introduction sheaths, are employed for a variety of diagnostic and surgical procedures, such as laparoscopy, arthroscopy, gynoscopy, thoracoscopy, cystoscopy, etc. Many of these procedures are carried out for purposes of tissue resection, which generally includes removal of tissue of an organ or a gland to treat tumors, infestations, and the like. In particular, such procedures may be carried out by inserting an introduction sheath into a patient's body through a surgical incision, or via natural anatomical orifices (e.g., mouth, vagina, and/or rectum), and performing the procedure or operation.

Snares, in particular, have been used in many medical procedures, including Endoscopic Mucosal Resection (EMR) and Endoscopic Sub-mucosal Resection (ESR), polypectomy, mucosectomy, etc., for resecting tissue from a target site. A snare device generally includes a snare loop formed by, e.g., snare wires, which engage the tissue intended to be resected. The snare loop is controlled and operated at a proximal end of the device through a suitable actuating mechanism. Tissue resection may be performed through a process widely known and referred to as electro-resectioning, which may be carried out by the snare. Typically, removal of tissue through methods such as electro-resectioning includes application of a cauterization voltage to the snare, which functions as an electrode.

In certain cases, it may be challenging to align the snare precisely with the tissue to be resected. Users of certain existing snare devices may rotate the handle of the device, attempting to cause a corresponding rotation of the snare. However, rotating the handle may rotate the outer shaft of the snare device, instead of isolating the rotation to the snare loop. Furthermore, rotation of the entire handle may be cumbersome for the user or not transfer the rotation to the distal end of the device.

SUMMARY

Embodiments of the present disclosure relate to, among other things, a rotatable medical device. Each of the embodiments disclosed herein may include one or more of the features described in connection with any of the other disclosed embodiments.

In one example, a medical device may include a handle, a sheath fixed relative to the handle, a longitudinal actuator movable relative to the handle, an end effector, a member extending proximally from the end effector through the sheath, with a portion of the member being fixed relative to the longitudinal actuator, and a rotation actuator. Movement of the rotation actuator may cause rotation of the member relative to the sheath, and movement of the longitudinal actuator may cause longitudinal movement of the member relative to the rotation actuator.

Any examples of medical devices described herein may additionally or alternatively include one or more of the following features: the end effector may be configured to conduct current to tissue during longitudinal movement of the longitudinal actuator and during rotation of the rotation actuator; the rotation actuator may be fixed in a longitudinal position relative to the sheath; when the longitudinal actuator is in a distal-most position, the rotation actuator may be positioned distal to the longitudinal actuator; the device may further comprise a rotation shaft around a portion of the member, the rotation shaft may include a non-circular cross-sectional shape, and an interior lumen of the rotation actuator may include the same non-circular cross-sectional shape; a distal portion of the rotation shaft may include the non-circular cross-sectional shape, and a proximal portion of the rotation shaft may include a different cross-sectional shape; distal movement of the longitudinal actuator may cause distal movement of the end effector; the member may extend through a lumen of the rotation actuator and may be fixed in an angular direction relative to the rotation actuator; the longitudinal actuator may include an electrical connector to connect the member to an electricity source; the member may be rotatable relative to the electrical connector; the handle may include an opening proximate a proximal end of the handle and a shaft distal to the opening, and the longitudinal actuator may be slidable along the shaft; when the longitudinal actuator is in a distal-most position, the end effector may extend from a distal end of the sheath; when the longitudinal actuator is in a proximal-most position, the end effector may be fully retracted within the sheath; the end effector may include a snare; and the member may be a wire.

In another example, a medical device may include a handle; a sheath fixed relative to the handle; a rotation actuator rotatable relative to the sheath and fixed in a longitudinal position relative to the sheath; a snare; a snare wire extending proximally from the snare through the sheath and through a lumen of the rotation actuator, wherein the snare wire is fixed in an angular position relative to the rotation actuator and movable in a longitudinal direction relative to the rotation actuator; and a longitudinal actuator configured to move relative to the handle to translate the snare wire along the longitudinal axis relative to the rotation actuator.

Any examples of medical devices described herein may additionally or alternatively include one or more of the following features: the longitudinal actuator may include an electrical connector to connect the snare wire to an electricity source; the snare wire may be rotatable relative to the electrical connector; the snare wire may be configured to be electrically connected to the electricity source during movement of the longitudinal actuator and during rotation of the rotation actuator; the device may further comprise a rotation shaft around a portion of the snare wire, the rotation shaft may include a non-circular cross-sectional shape, and the lumen of the rotation actuator may include the same non-circular cross-sectional shape; when the longitudinal actuator is in a distal-most position, the rotation actuator may be positioned distal to the longitudinal actuator; when the longitudinal actuator is in a distal-most position, the snare may extend from a distal end of the sheath and may include a first side and a second side defining an enclosed region between the first and second sides; and distal movement of the longitudinal actuator may cause distal movement of the snare.

In yet another example, a method for resecting tissue may include translating a longitudinal actuator along a longitudinal axis of a device, relative to a handle of the device, to cause an end effector to translate along the longitudinal axis relative to the handle; and rotating a rotation actuator around the longitudinal axis, relative to the handle, to cause the end effector to rotate relative to the handle. A member may extend proximally from the end effector through a sheath, the sheath being fixed relative to the handle. The rotation actuator may be fixed in a longitudinal position relative to the sheath, and the member may be fixed in an angular position relative to the rotation actuator and movable in a longitudinal direction relative to the rotation actuator.

Any method described herein may include one or more of the following features or steps: the rotation actuator may be rotated relative to the longitudinal actuator; distal movement of the longitudinal actuator may cause distal movement of the snare; and the method may further include using the end effector to apply a current to tissue.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

The present disclosure is drawn to rotatable medical devices and methods for using the rotatable medical devices. This disclosure will describe an example of a rotatable medical device that is a snare device, including a snare loop as an end effector. The principles of this disclosure apply, however, to other medical devices having end effectors other than a snare loop, including graspers, biopsy jaws, scissors, or others.

In general, the snare devices of this disclosure include a snare (e.g., a snare loop) that can be rotated around a longitudinal axis of the device relative to an outer sheath of the snare device. The snare also may be extended from and retracted into the outer sheath. Electro-resection of tissue using the snare may be carried out, even during rotation of the snare and proximal/distal movement of the snare.

Figure 1:
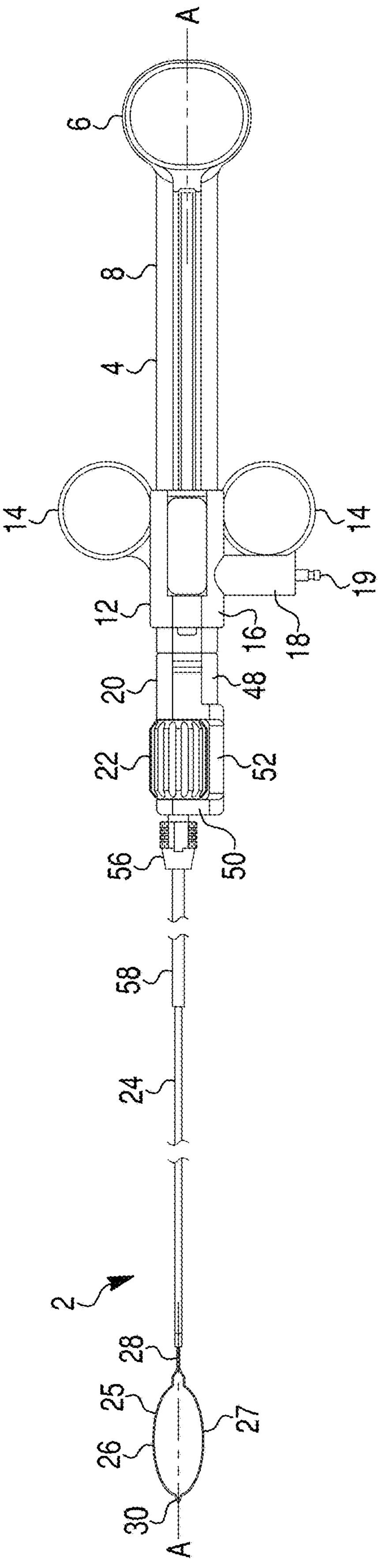
FIG. 1 illustrates a snare device with the snare in an extended position, according to an exemplary embodiment.
Figure 2:
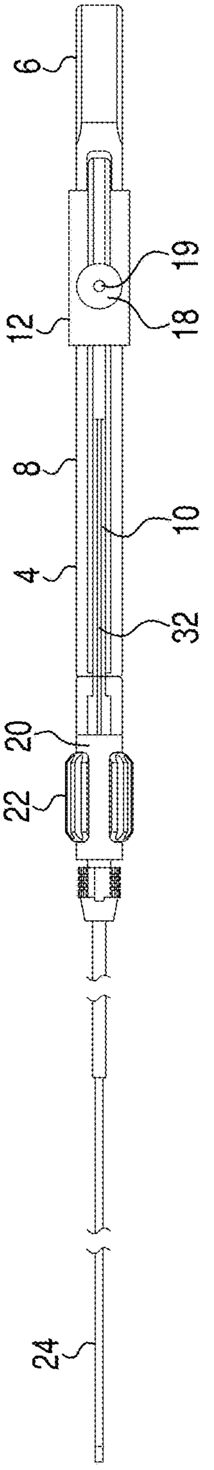
FIG. 2 illustrates a bottom view of the snare device of FIG. 1 with the snare in a retracted position, according to an exemplary embodiment.

Referring to FIGS. 1 and 2, a snare device 2 includes a longitudinal axis A extending from a proximal end of the device to a distal end of the device. A handle 4 may be positioned towards the proximal end of device 2 and may be fixed, through various components, relative to an outer sheath 24 of device 2. Handle 4 may include a finger opening 6 and an elongated shaft 8. During use, finger opening 6 may receive a user's thumb. Elongated shaft 8 may have a circular, oval, or any other exterior shape and may define an interior lumen. The interior lumen may receive a snare wire 28, portions of a longitudinal actuator 12, and other components to be described further below. Handle 4 further may include a slot 10 extending parallel to axis A that receives a radially inward protrusion of longitudinal actuator 12, allowing longitudinal actuator 12 to slide proximally and distally with respect to handle 4.

At its distal end, handle 4 may be connected to a rotation actuator connector 20, which houses a rotation actuator 22. Rotation actuator connector 20 may include a proximal opening (not shown) that receives distal protrusions (not shown) of handle 4. The proximal opening of rotation actuator connector 20 may be secured to the distal protrusions of handle 4 by a snap-fit, friction-fit, using adhesive, or by any other mechanism suitable for securing two components. Alternatively, handle 4 and rotation actuator connector 20 may be integrally formed as a single component.

Longitudinal actuator 12 may include at least one finger opening 14, an elongated shaft 16, and a lateral extension 18. During use, the one or more finger openings 14 (e.g., two finger openings 14) may each receive a user's finger. Elongated shaft 16 may be a hollow shaft that extends along axis A and fits around handle 4. As noted above, an interior of shaft 16 may include a protrusion that extends into slot 10 of handle 4. Longitudinal actuator 12 may therefore translate relative to handle 4. However, the protrusion of shaft 16 into slot 10 of handle 4 may act to prevent longitudinal actuator 12 from rotating relative to handle 4. Lateral extension 18 may house an electrical connector 19, to be described below. The various components of longitudinal actuator 12 may be integrally formed or may be separate components secured together by any method known in the art. As also described further below, a portion of a snare wire 28 may be fixed relative to longitudinal actuator 12.

Still referring to FIG. 1, device 2 further includes a snare 26, which may be connected to or continuous with a snare wire 28. Snare 26 may include a first side 25 and a second side 27, which may generally form a loop that defines an enclosed region. The first and second sides 25, 27 may each be curved and may connect and/or contact each other at a proximal end of snare 26 and at a distal tip 30. In one example, the loop of snare 26 may have a vesica piscis shape (e.g., a football shape), although there may be irregularities near the proximal and distal ends of snare 26, or anywhere in between. The enclosed region defined by snare 26 may be an opening that receives tissue during a medical procedure.

First and second sides 25, 27 of snare 26 may be formed from two separate wires connected to or contacting each other at their proximal and distal ends, or from a single wire. If snare 26 is formed from a single wire, the single wire may include a connection or contact between ends of the wire proximate the proximal end of snare 26, and the distal tip of snare 26 may be continuous and formed from the unbroken wire. As used herein, the term "wire" means any elongated member capable of translating within outer sheath 24. Furthermore, "wire" may technically refer to a bundle of individual wires or elongated members that are electrically or physically connected and therefore act as a single wire, such that a snare 26 formed of a single "wire" may be formed from a bundle of continuous wires, a cable, or any other elongate member. A snare 26 formed of two "wires" therefore may be formed by two separate bundles of wires that are connected to and/or contact each other proximate the proximal end of snare 26 and at distal tip 30.

The two sides 25, 27 of snare 26 (see FIG. 1) may join together and extend proximally to form snare wire 28. In an alternative example, the two sides 25, 27 of snare 26 may end at a location proximal to snare 26 but may be electrically connected to and secured to a separate snare wire 28.

Figure 3:
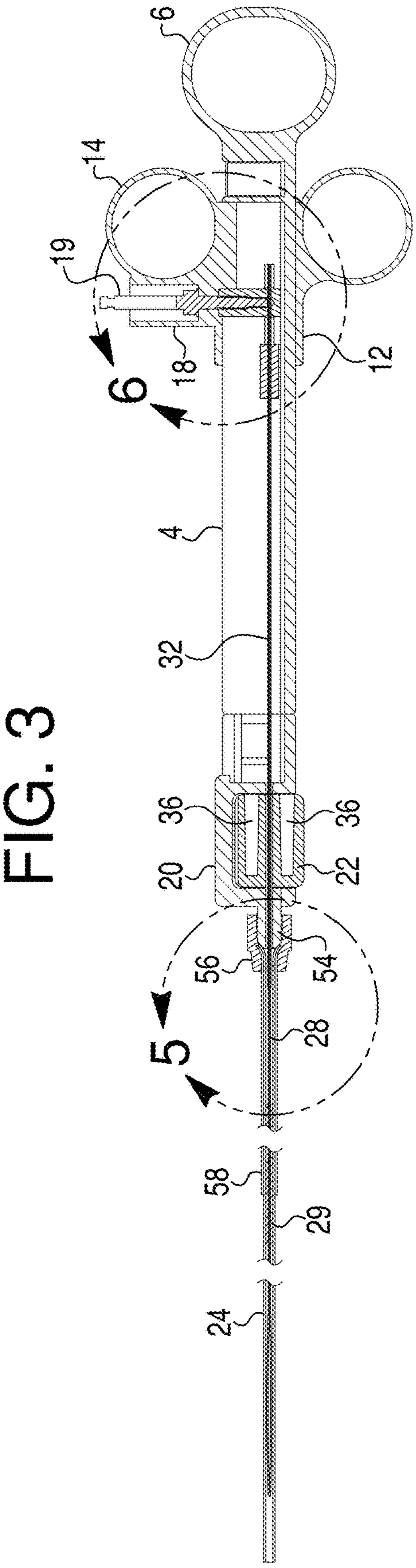
FIG. 3 illustrates a cross-sectional view of the snare device of FIG. 1, with the snare having been turned 180° around its longitudinal axis relative to FIG. 1, according to an exemplary embodiment.

Referring to FIG. 3, which illustrates a cross-sectional view of device 2, snare wire 28 may extend through an interior lumen of rotation actuator 22. Portions of snare wire 28 may be enclosed by a rotation shaft 32. A portion of snare wire 28, such as a proximal end of snare wire 28, may be fixed relative to longitudinal actuator 12, such that movement of longitudinal actuator 12 causes snare wire 28 and snare 26 to move in a corresponding manner along axis A relative to various other components of the device 2 (e.g., relative to sheath 24, rotation actuator 22, and handle 4). For example, distal movement of longitudinal actuator 12 relative to handle 4 may cause distal movement of snare wire 28 and snare 26, and proximal movement of longitudinal actuator 12 relative to handle 4 may cause proximal movement of snare wire 28 and snare 26. The connection of snare wire 28 to longitudinal actuator 12 will be described in more detail in connection with FIG. 6.

Figure 5:
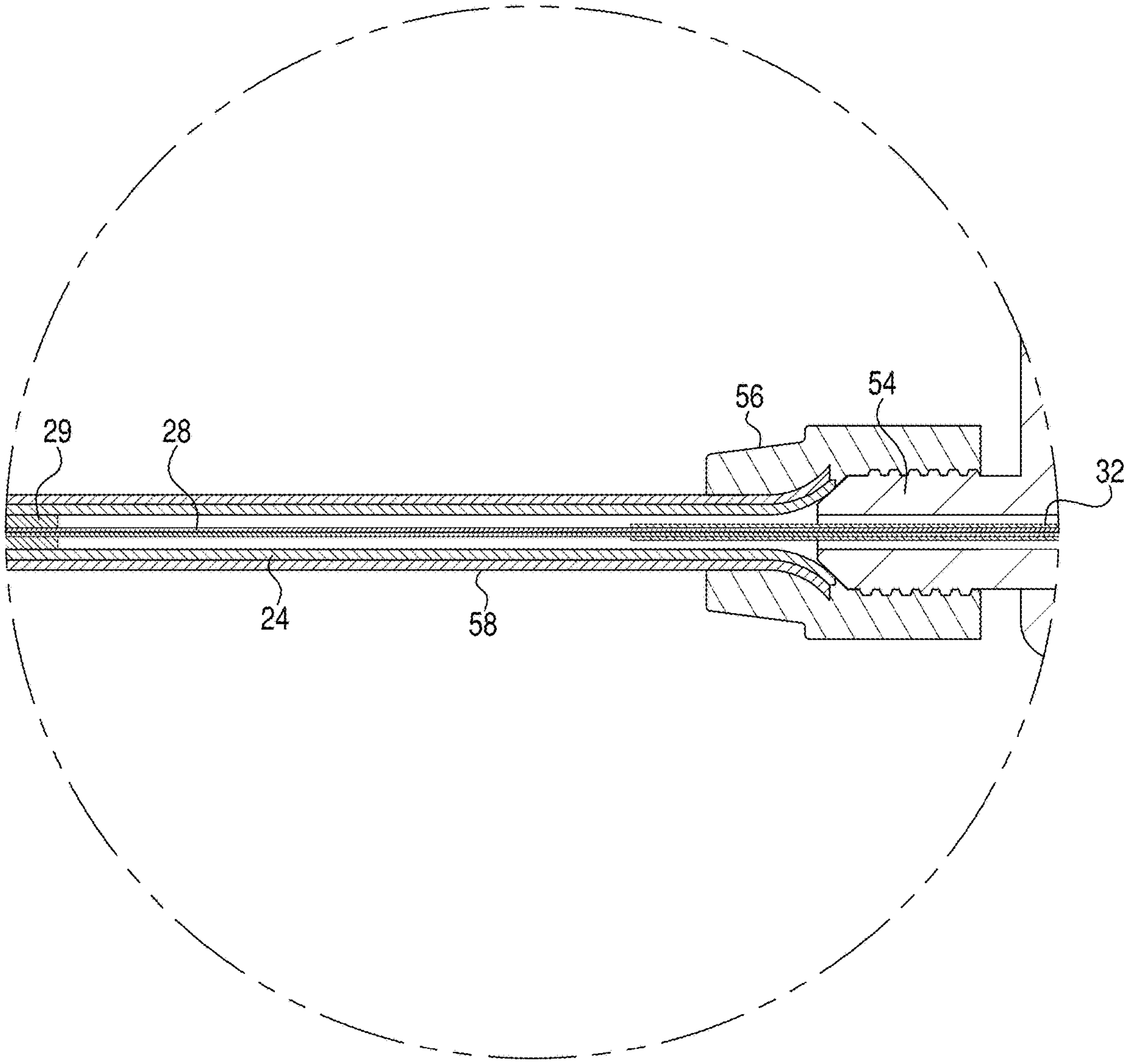
FIG. 5 illustrates a cross-sectional view of the snare wire, a rotation shaft, and an inner sheath within an outer sheath of the snare device, according to an exemplary embodiment.
Figure 6:
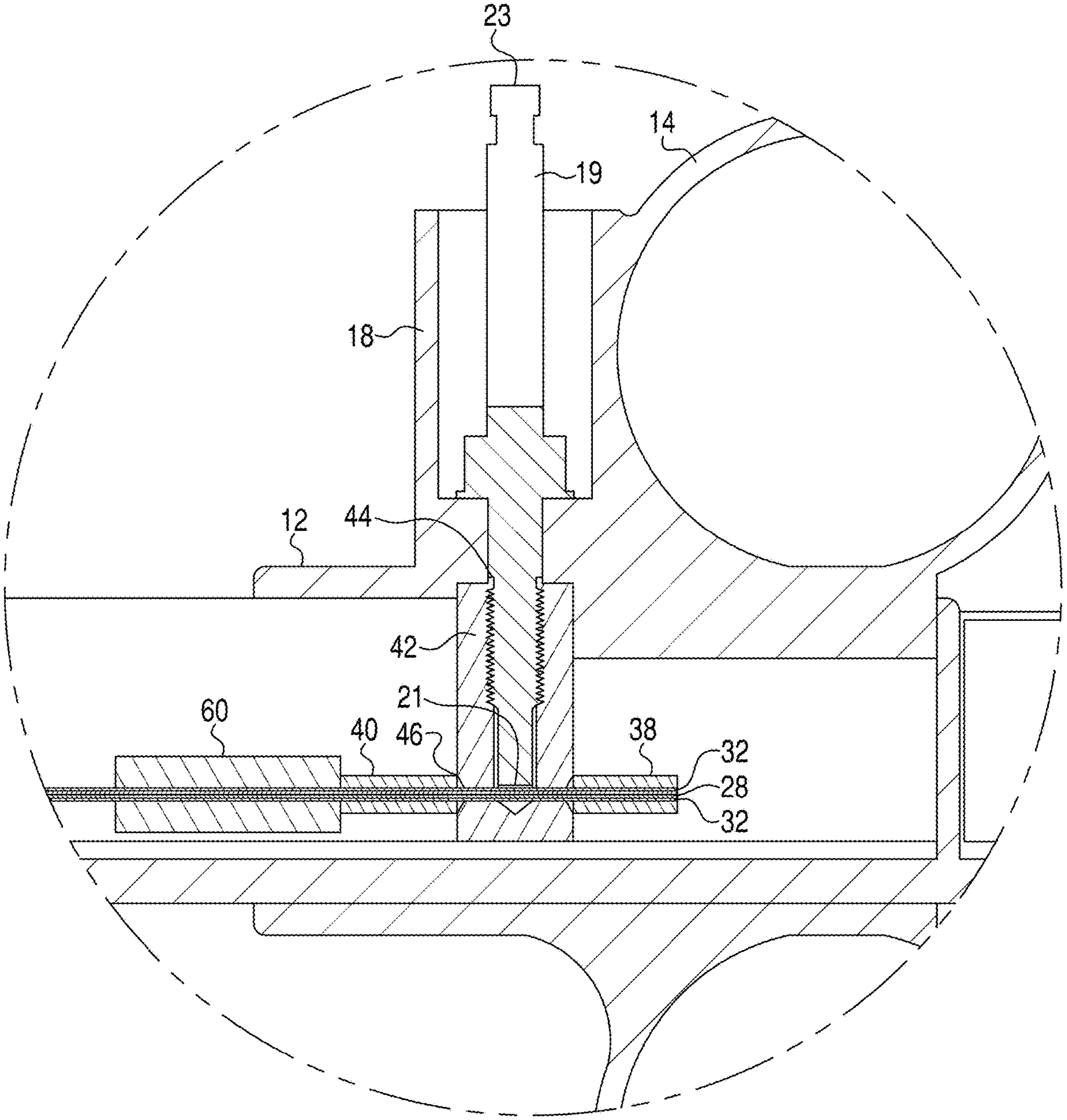
FIG. 6 illustrates a cross-sectional view of the electrical connection between a snare wire and a connector leading to an electricity source.

Referring to FIGS. 3, 5, and 6, portions of snare wire 28 may be surrounded by a rotation shaft 32. Rotation shaft 32 may be fixed relative to snare wire 28 by crimping, adhesive, or any other suitable attachment method. Accordingly, rotation shaft 32 also is fixed relative to snare 26. In an alternative example, the proximal end of snare wire 28 is fixed to a distal end of rotation shaft 32 at a location distal to rotation actuator 22. Rotation shaft 32 then may travel proximally through rotation actuator 22 and to longitudinal actuator 12. Rotation shaft 32 may include a conductive material, such as a metal, to transmit electrical energy from an energy source to the snare wire 28 and snare 26.

Rotation shaft 32 may include a distal portion having a square or other non-circular cross-sectional shape. For example, the cross-sectional shape may be oval, triangular, rectangular, or other polygonal shape. In another example, the cross-sectional shape of rotation shaft 32 may be partially circular with one or more radially outward protrusions or inward protrusions. The one or more protrusions may be a single symmetrical protrusion, an elongated protrusion extending parallel to the longitudinal axis, or ribs (e.g., multiple outward or inward protrusions extending along various lines parallel to the longitudinal axis). The cross-sectional shape of the distal portion of rotation shaft 32 may correspond to the cross-sectional shape of the interior lumen 34 of rotation actuator 22 (see FIGS. 4A and 4B, in which interior lumen 34 has a square cross-sectional shape corresponding to a square rotation shaft 32). In another example, if rotation shaft 32 includes one or more radially outward or inward protrusions, interior lumen 34 may have one or more corresponding slots or protrusions, respectively, extending parallel to longitudinal axis A.

The snare wire 28 itself may include any of the characteristics of the rotation shaft 32 described herein and/or may be integrally formed with the rotation shaft 32. For example, at least a portion of snare wire 28 may have a cross-sectional shape corresponding to the cross-sectional shape of an interior lumen of the rotation actuator, or the snare wire 28 may have different cross-sectional shapes along different lengths.

At a location proximal to rotation actuator 22, the cross-sectional shape of rotation shaft 32 may transition from a first shape to a second shape. For example, the cross-sectional shape may be a square shape along a section that passes through rotation actuator 22 and may transition to a circular shape along a proximal portion of rotation shaft 32. Referring to FIG. 6, the circular portion of rotation shaft 32 may allow the snare wire 28 and rotation shaft 32 to rotate freely (upon rotation of rotation actuator 22) relative to an electrical connector 19 while maintaining electrical contact with electrical connector 19.

Figure 4B:
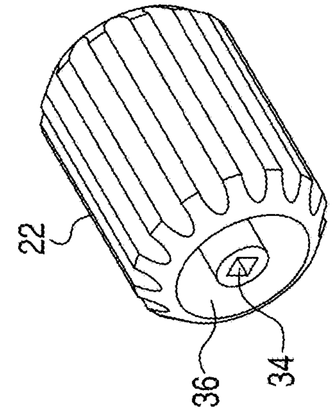
FIGS. 4A and 4B illustrate perspective views of the rotatable knob of the snare device of FIG. 1, according to an exemplary embodiment.
Figure 4A:
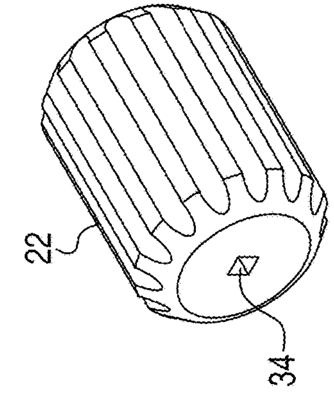

Rotation actuator 22 may be positioned distal to longitudinal actuator 12, even when longitudinal actuator 12 is in its distal-most position relative to handle 4. Referring to FIGS. 4A and 4B, rotation actuator 22 may be a substantially cylindrical knob extending along axis A, although rotation actuator 22 may have any cross-sectional shape. Rotation actuator 22 may have ribs along its exterior, also extending parallel to axis A, to aid in gripping by the user. As described previously, rotation actuator 22 may include an interior lumen 34 having a non-circular cross-sectional shape, or radially inward protrusions and/or radially outward slots, corresponding to the outer shape of rotation shaft 32 that allows rotation shaft 32 to slide (translate axially) relative to rotation actuator 22. In one example, interior lumen 34 has a square shape. Rotation actuator 22 may include a space between a portion of the material surrounding interior lumen 34 and the material of the exterior of rotation actuator 22. Although movable in an angular direction (e.g., rotatable) relative to handle 4 and outer sheath 24, rotation actuator 22 may be fixed in a longitudinal direction relative to handle 4 and outer sheath 24 via one or more components (e.g., rotation actuator connector 20).

Accordingly, when rotation actuator 22 is rotated about axis A relative to handle 4 and outer sheath 24, rotation shaft 32, snare wire 28, and snare 26 also rotate with respect to handle 4 and outer sheath 24. Snare wire 28 is therefore fixed in an angular direction relative to rotation actuator 22. However, rotation shaft 32 and snare wire 28 may be translatable proximally and distally (e.g., in a longitudinal direction) relative to rotation actuator 22. For example, a square rotation shaft 32 could translate or slide relative to a square interior lumen 34, or a rotation shaft 32 with ribs could translate within an interior lumen 34 having corresponding slots.

Referring to FIG. 1, rotation actuator connector 20 may include a proximal portion 48 adjacent to handle 4 and proximal to rotation actuator 22, a distal portion 50 distal to rotation actuator 22, and a connecting bar 52 to connect the proximal and distal portions 48, 50. The proximal and distal portions 48, 50 may prevent rotation actuator 22 from moving proximally or distally when snare wire 28 is moved proximally or distally by longitudinal actuator 12. Connecting bar 52 may extend parallel to axis A and exterior to rotation actuator 22, serving to connect proximal and distal portions 48, 50 while allowing the user to access rotation actuator 22.

Referring to FIGS. 3 and 5, a distal portion 54 of rotation actuator connector 20 may include threads and may be fixed to a shaft connector 56. In another embodiment, the rotation actuator connector 20 may be integrally formed with the shaft connector 56. The shaft connector 56 may be fixed to a connector sheath 58, which may extend around a proximal portion of outer sheath 24. The connector sheath 58 may provide additional rigidity to the proximal portion of outer sheath 24 and may strengthen the connection between outer sheath 24 and rotation actuator connector 20.

Referring to FIG. 5, rotation shaft 32 can be seen extending to a position distal to shaft connector 56. From the distal end of rotation shaft 32, snare wire 28 may continue to extend distally. An inner sheath 29 may be positioned within outer sheath 24 distal to rotation shaft 32. Inner sheath 29 may fill space between outer sheath 24 and snare wire 28 to help prevent bunching of snare wire 28, while still allowing snare wire 28 to freely rotate and move in proximal and distal directions. Accordingly, inner sheath 29 may be fixed relative to one of outer sheath 24 or snare wire 28. Alternatively, inner sheath 29 may be free-floating within outer sheath 24 and unfixed to either outer sheath 24 or snare wire 28. In one example, inner sheath 29 may be integrally formed with outer sheath 24 and may define a region of outer sheath 24 having a decreased inner diameter.

FIG. 6 illustrates the electrical components of device 2 that allow snare 26 to be used for electro-resection. Lateral extension 18 of longitudinal actuator 12 holds electrical connector 19. Electrical connector 19 may be elongated with its axis aligned perpendicular to axis A. A first, interior end 21 of electrical connector 19 may be positioned proximate to an exterior of rotation shaft 32. Connector 19 may be coupled to an insert 42, described below, or formed integrally with insert 42. A second, exterior end 23 of electrical connector 19 may be connected through wires or other mechanisms known in the art (not shown) to a source of electricity, such as a generator (not shown).

First end 21 of connector 19 may be positioned within insert 42, which may be fixed relative to longitudinal actuator 12 or may be integrally formed with longitudinal actuator 12. Insert 42 may include an opening 44 to receive the connector 19. Opening 44 may extend from an exterior end of insert 42 towards axis A of device 2. A portion of electrical connector 19 proximate the first end 21 may be threaded to secure connector 19 to insert 42 within opening 44. Insert 42 may include a through-hole 46 that extends parallel to axis A. Snare wire 28 and rotation shaft 32 may be received within through-hole 46. Because rotation shaft 32 is cylindrical along its proximal portion, rotation shaft 32 may freely rotate relative to insert 42 while maintaining electrical contact with insert 42, and therefore with electrical connector 19.

Proximal and distal to connector 42, tubular members 38, 40 may be secured to the exterior of rotation shaft 32. Tubular members 38, 40 may be fixed (e.g., by crimping, adhesive, or any other mechanism) to rotation shaft 32 and may prevent longitudinal movement of snare wire 28 relative to connector 42 and longitudinal actuator 12. Accordingly, when longitudinal actuator 12 is moved proximally or distally, snare wire 28 and snare 26 correspondingly move proximally or distally. However, because rotation shaft 32 has a smaller diameter than the diameter of through-hole 46, snare wire 28 and snare 26 can rotate relative to longitudinal actuator 12 regardless of the proximal/distal position of longitudinal actuator 12.

A stopper 60 may be positioned distal to tubular member 40. Stopper 60 may be an elongated, tubular member having an interior lumen that receives snare wire 28 and rotation shaft 32. Stopper 60 may be fixed relative to rotation shaft 32. Different devices 2 may include different sized stoppers depending on the desired extension of snare 26 from the distal end of outer sheath 24. For example, a shorter stopper 60 (or a stopper 60 positioned more proximally on rotation shaft 32) may allow the snare 26 to extend farther from the distal end of outer sheath 24 when longitudinal actuator 12 is pushed as far distally as possible. In contrast, a longer stopper 60 (or a stopper 60 positioned more distally on rotation shaft 32) may prevent the snare 26 from extending as far from the distal end of outer sheath 24 when longitudinal actuator 12 is pushed distally. When longitudinal actuator 22 is in its most distal position, the distal end of stopper 60 may contact a surface of handle 4 defining a distal end of the lumen within handle 4.

During a medical procedure, device 2 may be used to resect tissue. Device 2 may be inserted into a patient with snare 26 in a retracted position, as shown in FIGS. 2 and 3. In one example, the outer sheath 24 containing snare 26 may be inserted through a working channel of an endoscope or other tool. In the retracted position of snare 26, longitudinal actuator 12 may be in proximal position relative to handle 4. When the user desires to extend snare 26, the user may push longitudinal actuator 12 in a distal direction. Snare wire 28 is then pushed distally as well, causing snare 26 to extend from the distal end of outer sheath 24. Longitudinal actuator 12 may be pushed distally until stopper 60 abuts the distal end of the lumen within handle 4.

The user may position snare 26 around tissue to be resected. To help position snare 26 accurately, the user may rotate rotation actuator 22 to cause snare 26 to turn, or rotate about axis A. Rotation actuator 22, and therefore snare 26, may be rotated both clockwise and counter-clockwise. In one example, snare 26 may be positioned at any angular position. In another example, snare 26 may be positioned in a finite number of predefined angular positions, such as four different positions each about 90° from adjacent positions.

If the user desires to conduct electro-resection, the electricity source can be turned on to send electrical energy through connector 19 to rotation shaft 32 and snare wire 28. Rotation shaft 32, snare wire 28, and snare 26 may all be electrically connected. The user may pull longitudinal actuator 12 proximally during application of electrical energy to the tissue such that snare 26 tightens around and cuts tissue to be removed. Electrical energy may be continued to be applied to the tissue, even when snare 26 is rotated or moved proximally or distally. Once cut, the tissue may be removed from the patient using tools through a working channel of an endoscope or other medical device.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A medical device, comprising:

a handle;

an outer sheath extending distally from the handle;

an end effector;

a member extending proximally from the end effector and slidably disposed in the outer sheath;

an inner sheath fixed to an exterior surface of the member, wherein the inner sheath is positioned circumferentially between an interior surface of the outer sheath and the exterior surface of the member, wherein the inner sheath is configured to inhibit lateral movement of the member within the outer sheath; and a rotation actuator coupled to the member and movable relative to the handle in a clockwise direction and a counter-clockwise direction, wherein rotation of the rotation actuator causes rotation of the member relative to the outer sheath in at least one of the clockwise direction or the counter-clockwise direction.

2. The medical device of claim 1, further comprising:

a longitudinal actuator coupled to the member and movable relative to the handle in a distal direction and a proximal direction, wherein movement of the longitudinal actuator causes movement of the member relative to the rotation actuator in at least one of the distal direction or the proximal direction.

3. The medical device of claim 2, further comprising:

a stopper positioned within the handle and coupled to a portion of the member, wherein the stopper is configured to abut against the rotation actuator to limit distal movement of the end effector relative to the outer sheath, wherein a longitudinal length of the stopper defines a limit of distal movement of the end effector relative to the outer sheath.

4. The medical device of claim 1, further comprising:

a rotation shaft slidably disposed in a lumen defined by the rotation actuator and coupled to a portion of the member, wherein the rotation shaft includes at least one portion having a non-circular cross-sectional shape that is complementary to a non-circular cross-sectional shape of the lumen of the rotation actuator.

5. The medical device of claim 4, wherein the rotation shaft includes a distal portion having the non-circular cross-sectional shape, and a proximal portion having a different cross-sectional shape.

6. The medical device of claim 1, wherein the handle includes a distal end having at least one distal protrusion, and wherein the rotation actuator includes at least one proximal opening configured to receive the at least one distal protrusion and longitudinally fix the rotation actuator relative to the handle.

7. The medical device of claim 1, wherein the end effector includes a snare that is configured to conduct current to tissue.

8. A medical device, comprising:

a handle;

an outer sheath extending distally from the handle;

an end effector;

a member extending proximally from the end effector through the outer sheath; and an inner sheath disposed within the outer sheath and positioned over an exterior surface of the member, wherein the inner sheath is detached from and floats freely between an interior surface of the outer sheath and the exterior surface of the member.

9. The medical device of claim 8, further comprising a rotation actuator coupled to a distal end of the handle, wherein the rotation actuator is configured to rotate the member relative to the outer sheath.

10. The medical device of claim 9, further comprising:

a rotation connector having a proximal opening configured to receive at least one protrusion at the distal end of the handle, wherein the rotation connector is longitudinally fixed relative to the handle and the outer sheath, and configured to house the rotation actuator therein.

11. The medical device of claim 9, further comprising a rotation shaft coupled to the rotation actuator and to the member.

12. The medical device of claim 11, wherein the rotation actuator defines a lumen having a non-circular cross-sectional shape, and wherein the rotation shaft includes at least one portion having a non-circular cross-sectional shape that is complementary to the lumen of the rotation actuator.

13. The medical device of claim 8, further comprising a stopper fixed to the member and positioned proximal to the outer sheath, wherein a length of the stopper limits distal movement of the end effector relative to the outer sheath.

14. The medical device of claim 8, further comprising a longitudinal actuator movable relative to the handle in a distal direction and a proximal direction, wherein a portion of the member is fixed relative to the longitudinal actuator.

15. The medical device of claim 8, wherein the inner sheath is fixed to the exterior surface of the member.

16. A medical device, comprising:

a handle;

an outer sheath extending distally from the handle;

an end effector;

a member extending proximally from the end effector through the outer sheath;

an inner sheath disposed within the outer sheath and positioned over an exterior surface of the member, wherein the inner sheath is configured to inhibit lateral movement of the member within the outer sheath;

a rotation actuator movable relative to the handle in a clockwise direction and a counter-clockwise direction; and a rotation shaft slidably disposed in a lumen defined by the rotation actuator, and coupled to a portion of the member, wherein the rotation shaft includes at least one portion having a non-circular cross-sectional shape that is complementary to a non-circular cross-sectional shape of the lumen of the rotation actuator, wherein rotation of the rotation actuator causes rotation of the member relative to the outer sheath in the clockwise direction or the counter-clockwise direction.

17. The medical device of claim 16, further comprising:

a longitudinal actuator movable relative to the handle in a distal direction and a proximal direction; and a stopper coupled to the member and received within the handle, wherein translation of the longitudinal actuator causes translation of the member relative to the rotation actuator, wherein a longitudinal length of the stopper defines a limit of distal movement of the end effector relative to the outer sheath, wherein the stopper is configured to abut against the rotation actuator to limit distal movement of the end effector relative to the outer sheath, and whereon the inner sheath is fixed to the exterior surface of the member.

18. A medical device, comprising:

a handle;

an outer sheath extending distally from the handle;

an end effector including a snare configured to conduct current to tissue;

a member extending proximally from the end effector and slidably disposed in the outer sheath; and an inner sheath fixed to an exterior surface of the member, wherein the inner sheath is positioned circumferentially between an interior surface of the outer sheath and the exterior surface of the member, and wherein the inner sheath is configured to inhibit lateral movement of the member within the outer sheath.

19. The medical device of claim 18, further comprising a rotation actuator coupled to a distal end of the handle, wherein the rotation actuator is configured to rotate the member relative to the outer sheath.

20. The medical device of claim 19, further comprising a rotation shaft coupled to the rotation actuator and to the member.

* * * * *